US006988798B1

(12) United States Patent
Duffie

(10) Patent No.: US 6,988,798 B1
(45) Date of Patent: Jan. 24, 2006

(54) FLEXIBLE EYEGLASS SIDE SHIELD

(76) Inventor: Ken Duffie, 121 Highland St., Middleboro, MA (US) 02532

( * ) Notice: Subject to any disclaimer, the term of this patent is extended or adjusted under 35 U.S.C. 154(b) by 0 days.

(21) Appl. No.: 10/751,848

(22) Filed: Jan. 6, 2004

Related U.S. Application Data

(60) Provisional application No. 60/439,155, filed on Jan. 10, 2003.

(51) Int. Cl.
G02C 7/10 (2006.01)

(52) U.S. Cl. .......................................... 351/44; 2/449
(58) Field of Classification Search ................. 351/41, 351/44, 158; 2/12, 13, 448–451
See application file for complete search history.

(56) References Cited

U.S. PATENT DOCUMENTS

| 5,113,529 | A | * | 5/1992 | Carr ................................. 2/13 |
| 5,388,269 | A | * | 2/1995 | Griffin ............................. 2/13 |
| 5,402,189 | A | * | 3/1995 | Gill ............................. 351/44 |
| 5,748,278 | A |   | 5/1998 | Simmons, Sr. |
| 5,781,271 | A |   | 7/1998 | Wheeler |
| 6,393,609 | B1 |  | 5/2002 | Simmons, Sr. |

* cited by examiner

Primary Examiner—Huy Mai
(74) Attorney, Agent, or Firm—John P. McGonagle

(57) ABSTRACT

Portable safety side shields made from a flexible plastic that will slip onto a wide variety of eyeglasses. An eyeglass temple piece is weaved through slots in the side of a side shield for attachment to the wearer's temple. The slots in the side shield are long enough to allow attachment to eyeglasses with different pantoscopic angles. The side shield overlaps the front portion of an eyeglass frame, sealing the side shield against the eyeglass frame and preventing the side shield from sliding backward.

14 Claims, 2 Drawing Sheets

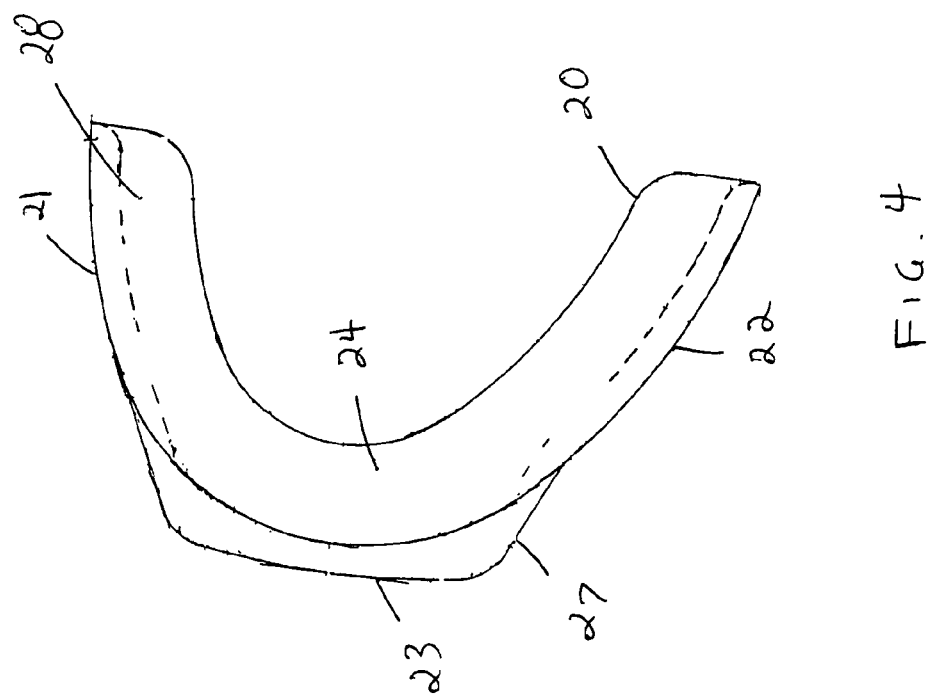
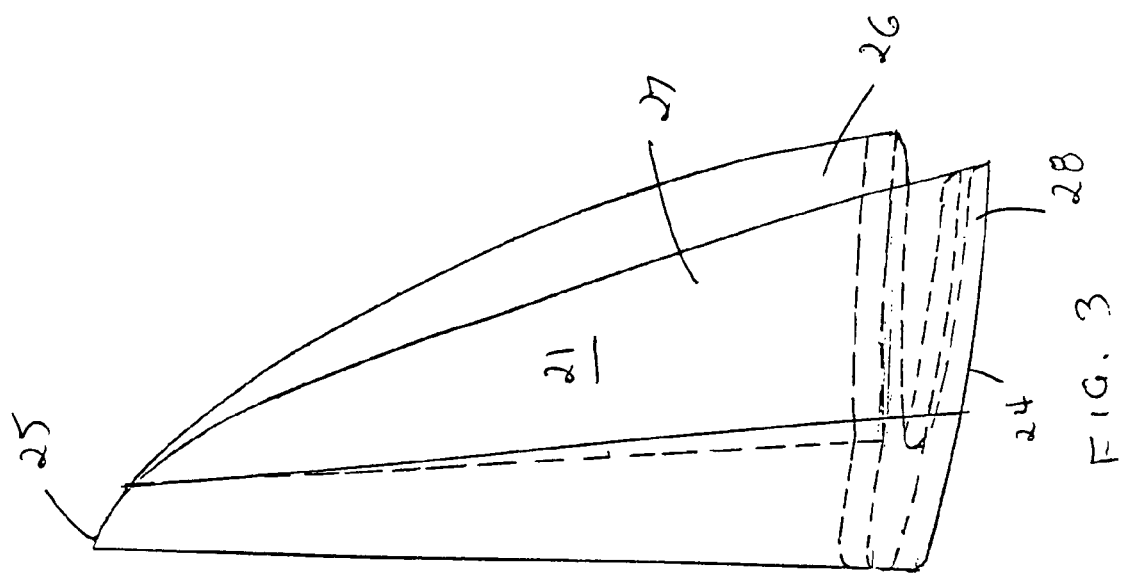

FLEXIBLE EYEGLASS SIDE SHIELD

RELATED U.S. APPLICATION DATA

This application claims the benefit of Provisional Application 60/439,155, filed Jan. 10, 2003.

BACKGROUND OF THE INVENTION

This invention relates to safety glasses, and in particular, to portable, flexible, eyeglass safety side shields.

In prior years, workers in environments that could be hazardous to the eyes were required to wear safety goggles which covered the face about the eyes, and which were cumbersome to the wearer to the point of being a distraction from the work to be done. The goggles further created vision aberrations that made the workers' task even harder, particularly when the goggles were fitted over prescription eyeglasses.

In view of the above, a migration toward the use of safety eyeglasses has occurred. Safety glasses are well known in the prior art and are used to protect the eyes of an individual from airborne particles, high-velocity projectiles, wind and the like. The use of safety glasses acceptable both for use in hazardous areas, and for casual wear, has given rise to the use of safety side shields. The safety side shields are added to eyeglasses to provide a protective barrier to the side, above or below the eye and normally supplements safety glasses.

Safety side shields for prescription glasses are known which are permanently fixed with metal brads, or are permanently molded as an integral part of ear pieces and eyeglass frames. While providing a more comfortable fit for work in hazardous areas, such glasses are too bizarre in appearance for casual wear. For regular daily wear, therefore, the user must purchase a second pair of prescription glasses.

To gain wider acceptance of the use of safety eyeglasses, portable safety side shields have become popular. Portable safety side shields may be easily mounted and detached from eyeglass frames. A wearer may mount the side shields on eyeglass frames when in a hazardous environment, and remove the side shields for casual every day wear.

Portable safety side shields are known in the prior art. Prior art safety shields typically partially overlap the side, front, and top of the eyeglass lens frame, and employ either metal fasteners or elastic bands with metal tips to attach to the ear pieces of the eyeglass frames. These side shields are usually difficult to mount to eyeglass frames, and restrict temple movement so that it is difficult to fold the temples to store the eyeglasses in a shirt pocket or a spectacle case. Furthermore, the protection provided by such side shields is easily lost through slight inadvertent impact or rotational movement of the shields. Because of their metal conductive parts, prior art side shields create an electrical hazard when working in environments with high current electrical fields. In addition, the conducting parts are susceptible to chemical corrosion, and with deterioration may come apart during impact.

Many of the known safety side shields have a hinge window to accommodate a wide range of eye glass hinge sizes. Such hinge windows, however, will allow projectiles moving in a primarily horizontal direction to impact the eye.

Other portable safety side shields are made of plastic in an effort to remove conductive metallic parts from the safety side shields. The plastic portable safety side shields of the prior art are made from a stiffened plastic, typically with a fixed pantoscopic angle (the angle a temple eyeglass piece makes with the eyeglass front to which it is attached) molded into them that cannot be easily varied for eyeglasses with a different pantoscopic angle. Prior art rigid plastic portable safety side shields are also limited in size range and are not readily adapted to fit different spectacle sizes and shapes.

SUMMARY OF THE INVENTION

The present invention provides portable safety side shields made from a flexible plastic that will slip onto a wide variety of eyeglasses. The material of the present invention absorbs the energy of impact as opposed to rigid prior art materials requiring strength to repel impact. An eyeglass temple piece (ear piece) is weaved through slots in the side of the invention side shield for attachment to the wearer's temple. Being flexible, the side shield can adapt to a variety of eyeglass sizes and shapes. The curvature of the side shield is generally smaller than that of most common spectacles. When mounted, this allows the side shield to uniformly flex and conform to the outer periphery of the spectacles. The slots in the invention side shield are long enough to allow attachment of the side shield to eyeglasses with different temple attachment locations, ranging from above the center line of the side view of the spectacles to attachment locations below the center line, and different temple thicknesses. The slots are long enough to allow attachment to eyeglasses with different pantoscopic angles, i.e., tilt of the eyeglass frame. The invention provides full movement of temple pieces (open and closed) and accommodates eyeglasses that have spring hinges where the temple piece can flex outward. The present invention does not require secondary parts for attachment, i.e., screws, spring clips, metal fasteners, tubes, and the like. The present invention overlaps the front portion of an eyeglass frame, sealing the side shield against the eyeglass frame and preventing the invention side shield from sliding backward. The present invention will not shatter and has soft rounded edges should there be any contact with the wearer's face.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

FIG. 3 is a top view of the side shield.

FIG. 4 is a front view of the side shield.

DETAILED DESCRIPTION OF INVENTION

Figure 1:
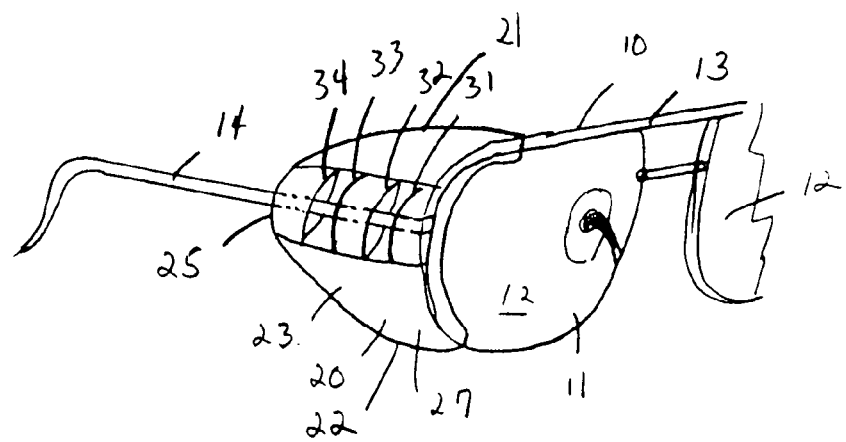
FIG. 1 is a partial perspective view of eyeglasses with an invention side shield.
Figure 2:
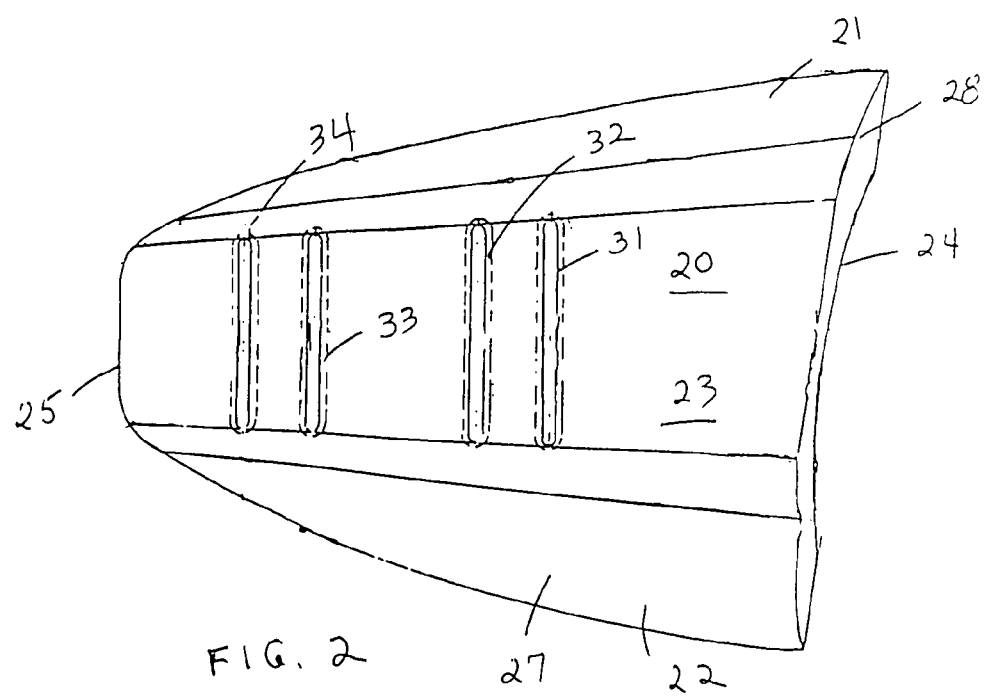
FIG. 2 is a side view thereof.

Referring to the drawings in detail wherein like elements are indicated by like numerals, there is shown a partial perspective view of a pair of eyeglasses 10 having flexible eyeglass side shields 20 removably attached to each side of the eyeglasses, said side shields 20 being constructed according to the principles of the present invention. The side shields 20 are injected molded from a flexible material. The eyeglasses 10 have a front portion 11 comprised of two lenses 12 and means 13 for holding the lenses 12. The means 13 for holding the lenses 12 may be a frame or a combination of a partial frame and holding threads. The eyeglasses 10 have two temple pieces 14 (a/k/a ear pieces) pivotally attached to said eyeglass front portion 11 on each side thereof for holding the eyeglass front portion 11 on the face of a user (eyeglass wearer).

The invention flexible eyeglass side shields 20 are removably attached on each side of the eyeglasses front portion 11 and have a front periphery 28 forming a semi-circle around the eyeglass lens 12 in front of the eye cavity of the user to provide at least partial eye protection on the top, bottom and side of the eye. Each side shield 20 is a generally arcuate-shaped shield, integrally formed as a single unit, and having a front periphery 28 for generally conforming to the shape of the individual eyeglass lens 12 or lens holding means 13. Each of the side shields 20 has a top portion 21, a bottom portion 22, a side portion 23, a front 24, a rear 25, an inside surface 26 and an opposite outside surface 27, said inside surface 26 being that portion of the side shield 20 facing the wearer, said front 24 and rear 25 defining a side shield horizontal longitudinal axis. The side shield side portion 23 has four parallel slots formed therein, a first slot 31 nearest the side shield front 24, a second slot 32 nearest the first slot 31, a fourth slot 34 nearest the side shield rear 25, and a third slot 33 between the second slot 32 and the fourth slot 34, each said slot having a longitudinal axis transverse to the side shield horizontal longitudinal axis, said slots opening through the outside surface 27 to and through the inside surface 26.

Each side shield 20 is adapted to being fitted onto the eyeglasses wherein each said side shield front periphery 28 is fitted over the top and outer side of a lens 12 or lens holding means 13. Each temple piece 14 is placed against the side shield inside surface 26 wherein each temple piece is adapted to being inserted into the first slot 31, inside surface 26 to outside surface 27, and inserted next into the second slot 32, outside surface 27 to inside surface 26, and inserted into the third slot 33 inside surface 26 to outside surface 27, and inserted into the fourth slot 34, outside surface 27 to inside surface 26. The side shield top portion 21, bottom portion 22 and rear portion 25 have peripheries with soft rounded edges.

It is understood that the above-described embodiment is merely illustrative of the application. Other embodiments may be readily devised by those skilled in the art which will embody the principles of the invention and fall within the spirit and scope thereof.

I claim:

1. A flexible safety side shield removably attached to each side of a pair of eyeglasses, said eyeglasses having a front portion comprised of two lenses and means for holding the lenses, two temple pieces pivotally attached to said eyeglass front portion on each side thereof for holding the eyeglass front portion on the face of an eyeglass wearer, comprising:

a generally arcuate-shaped and flexible plastic shield, integrally formed as a single unit, and having a front periphery generally conforming to the shape of an individual lens holding means, said shield having a top portion, a bottom portion, a side portion, a front, a rear, an inside surface and an opposite outside surface, said inside surface being that portion of the shield facing the wearer, said front and rear defining a shield horizontal longitudinal axis, said shield side portion having a plurality of parallel slots formed therein, each said slot having a longitudinal axis transverse to the shield horizontal longitudinal axis, said slots opening through the outside surface to and through the inside surface.

2. A flexible safety side shield as recited in claim 1, wherein:

the shield is adapted to being fitted onto the eyeglasses wherein each said shield front has a periphery fitted over a top and outer side of a lens holding means;

wherein, a temple piece is placed against the shield inside surface and weaved through said parallel slots.

3. A flexible safety side shield as recited in claim 2, wherein:

the shield top portion, bottom portion and rear have peripheries with soft rounded edges.

4. A flexible safety side shield as recited in claim 3, wherein:

said shield is removably attached on a side of the eyeglasses front portion, said shield front periphery forming a semi-circle around an eyeglass lens in front of a user eye cavity.

5. A flexible safety side shield as recited in claim 4, wherein:

said plurality of parallel slots is comprised of a first slot nearest the shield front, a second slot nearest the first slot, a fourth slot nearest the shield rear, and a third slot between the second slot and the fourth slot.

6. A flexible safety side shield as recited in claim 5, wherein:

a temple piece is inserted into the first slot, shield inside surface to shield outside surface, and inserted next into the second slot, shield outside surface to shield inside surface, and inserted into the third slot, shield inside surface to shield outside surface, and inserted into the fourth slot, shield outside surface to shield inside surface.

7. A flexible safety side shield as recited in claim 6, wherein:

said shield front periphery has a curvature less than a curvature of said lens holding means.

8. A flexible safety side shield removably attached to each side of a pair of eyeglasses, said eyeglasses having a front portion comprised of two lenses and means for holding the lenses, two temple pieces pivotally attached to said eyeglass front portion on each side thereof for holding the eyeglass front portion on the face of an eyeglass wearer, comprising:

a generally arcuate-shaped and flexible plastic shield, integrally formed as a single unit, and having a front periphery generally conforming to the shape of an individual lens, said shield having a top portion, a bottom portion, a side portion, a front, a rear, an inside surface and an opposite outside surface, said inside surface being that portion of the shield facing the wearer, said front and rear defining a shield horizontal longitudinal axis, said shield side portion having a plurality of parallel slots formed therein, each said slot having a longitudinal axis transverse to the shield horizontal longitudinal axis, said slots opening through the outside surface to and through the inside surface.

9. A flexible safety side shield as recited in claim 8, wherein:

the shield is adapted to being fitted onto the eyeglasses wherein each said shield front has a periphery fitted over a top and outer side of a lens;

wherein, a temple piece is placed against the shield inside surface and weaved through said parallel slots.

10. A flexible safety side shield as recited in claim 9, wherein:
the shield top portion, bottom portion and rear have peripheries with soft rounded edges.

11. A flexible safety side shield as recited in claim 10, wherein:
said shield is removably attached on a side of the eyeglasses front portion, said shield front periphery forming a semi-circle around an eyeglass lens in front of a user eye cavity.

12. A flexible safety side shield as recited in claim 11, wherein:
said plurality of parallel slots is comprised of a first slot nearest the shield front, a second slot nearest the first slot, a fourth slot nearest the shield rear, and a third slot between the second slot and the fourth slot.

13. A flexible safety side shield as recited in claim 12, wherein:
a temple piece is inserted into the first slot, shield inside surface to shield outside surface, and inserted next into the second slot, shield outside surface to shield inside surface, and inserted into the third slot, shield inside surface to shield outside surface, and inserted into the fourth slot, shield outside surface to shield inside surface.

14. A flexible safety side shield as recited in claim 13, wherein:
said shield front periphery has a curvature less than a curvature of an individual lens.

* * * * *